(12) United States Patent
Boardman (10) Patent No.: US 10,539,693 B2
(45) Date of Patent: Jan. 21, 2020

(54) RADIONUCLIDE DETECTION AND IDENTIFICATION

(75) Inventor: David Boardman, Kirrawee (AU)

(73) Assignee: Australian Nuclear Science and Technology Organization, New South Wales (AU)

( * ) Notice: Subject to any disclaimer, the term of this patent is extended or adjusted under 35 U.S.C. 154(b) by 0 days.

(21) Appl. No.: 14/131,642

(22) PCT Filed: Jul. 6, 2012

(86) PCT No.: PCT/AU2012/000818
§ 371 (c)(1),
(2), (4) Date: Mar. 27, 2014

(87) PCT Pub. No.: WO2013/006898
PCT Pub. Date: Jan. 17, 2013

(65) Prior Publication Data
US 2014/0367582 A1    Dec. 18, 2014

(30) Foreign Application Priority Data

Jul. 8, 2011 (AU) .................. 2011902731

(51) Int. Cl.
*G01T 1/36* (2006.01)
*G01V 5/00* (2006.01)
(Continued)

(52) U.S. Cl.
CPC ............. *G01T 1/36* (2013.01); *G01N 23/00* (2013.01); *G01T 1/16* (2013.01); *G01V 5/0075* (2013.01); *G06K 9/6234* (2013.01)

(58) Field of Classification Search
CPC ........... G01T 1/36; G01T 1/16; G06K 9/6234; G01N 23/00; G01V 5/0075
See application file for complete search history.

(56) References Cited

U.S. PATENT DOCUMENTS 5,153,439 A    10/1992   Gozani et al.
5,572,624 A * 11/1996   Sejnoha .................. G10L 15/06
                                                      704/251

(Continued)

FOREIGN PATENT DOCUMENTS

CN          1509153 A     6/2004
CN          1556921 A    12/2004
(Continued)

OTHER PUBLICATIONS

Wu et al. Probability estimates for multi-class classification by pairwise coupling, Journal of Machine Learning Research vol. 5 (Aug. 2004), pp. 975-1005.*

(Continued)

*Primary Examiner* — David P Porta
*Assistant Examiner* — Shun Lee
(74) *Attorney, Agent, or Firm* — Kilpatrick Townsend & Stockton LLP (57) ABSTRACT

Described herein is a method of processing a gamma ray spectrum acquired from a target. The method comprises determining whether the gamma ray spectrum of the target belongs to a first class of a plurality of classes, the first class containing reference gamma ray spectra of one or more radionuclide sources of interest, using optimal loading coefficients associated with the one or more radionuclide sources of interest, wherein the optimal loading coefficients have been obtained using Fisher linear discriminant analysis, and generating an output signal dependent on the determining.

21 Claims, 6 Drawing Sheets

(51) Int. Cl.
*G01N 23/00* (2006.01)
*G01T 1/16* (2006.01)
*G06K 9/62* (2006.01)

(56) References Cited

U.S. PATENT DOCUMENTS

| | | | | |
|---|---|---|---|---|
| 6,405,065 B1* | 6/2002 | Malin | ............ | A61B 5/0075 |
| | | | | 128/923 |
| 6,778,704 B1* | 8/2004 | Kawatani | ............ | G06K 9/6807 |
| | | | | 382/159 |
| 7,961,956 B1 | 6/2011 | Minter | | |
| 2002/0009213 A1 | 1/2002 | Rowe et al. | | |
| 2004/0086078 A1 | 5/2004 | Adams et al. | | |
| 2007/0080297 A1 | 4/2007 | Clarke et al. | | |
| 2008/0040614 A1* | 2/2008 | Abe | ............ | G06K 9/00885 |
| | | | | 713/186 |

FOREIGN PATENT DOCUMENTS

| | | | |
|---|---|---|---|
| CN | 1948956 A | 4/2007 | |
| JP | 08-319879 A | 12/1996 | |
| JP | 2005512064 A | 4/2005 | |
| JP | 2006215704 A | 8/2006 | |
| JP | 2010061376 A | 3/2010 | |
| JP | 2011-100395 A | 5/2011 | |
| WO | 02/084605 A2 | 10/2002 | |
| WO | 2011/057339 A1 | 5/2011 | |
| WO | 2013/006898 A1 | 1/2013 | |

OTHER PUBLICATIONS

Fu et al. Learning Object Material Categories via Pairwise Discriminant Analysis, IEEE Conference on Computer Vision and Pattern Recognition (Jun. 2007), 7 pages.*

Kangas, Lars J., et al., "The use of artificial neural networks in PVT-based radiation portal monitors," Nuclear Instruments and Methods in Physics Research A, Jan. 19, 2008, vol. 587, No. 2-3, pp. 398-412.

Yoshida, E., et al. "Application of neural networks for the analysis of gamma-ray spectra measured with a Ge spectrometer." *Nuclear Instruments and Methods in Physics Research Section A: Accelerators, Spectrometers, Detectors and Associated Equipment*, vol. 484, No. 1 (2002), pp. 557-563.

Blackadar, J. M. et al. "Evaluation of Commercial Detectors," Los Alamos National Laboratory, Los Alamos, NM, Tech. Rep. LA-UR-03-4020, 2003, 9 pages.

Jolliffe, I. T. "Graphical Representation of Data Using Principal Components: Biplots." In: *Principal Component Analysis*, 2nd ed. (New York, Springer Science+Business Media, LLC, 2004), pp. 92-93.

Jolliffe, I. T. "Outlier Detection, Influential Observations and Robust Estimation: Detection of Outliers Using Principal Components." In: *Principal Component Analysis*, 2nd ed. (New York, Springer Science+Business Media, LLC, 2004), pp. 236-237.

Pibida, L., Unterweger, M., and Karam, L. R. "Evaluation of Handheld Radionuclide Identifiers." *Journal of Research of the National Institute of Standards and Technology*, vol. 109, No. 4 (2004), pp. 451-456.

Price, J. R., and Gee, T. F. "Face recognition using direct, weighted linear discriminant analysis and modular subspaces." *Pattern Recognition*, vol. 38, No. 2 (2005), pp. 209-219.

Fawcett, T. "An introduction to ROC analysis." *Pattern Recognition Letters*, vol. 27, No. 8 (2006), pp. 861-874.

Dragovic, S., and Onjia, A. "Classification of soil samples according to geographic origin using gamma-ray spectrometry and pattern recognition methods." *Applied Radiation and Isotopes*, vol. 65, No. 2 (2007), pp. 218-224.

ANSI N42.38-2006, American National Standard Performance Criteria for Spectroscopy—Based Portal Monitors Used for Homeland Security, IEEE, 3 Park Avenue, New York, Ny 10016-5997, USA, Jan. 2007, 52 pages.

Sullivan, C. J., et al. "Generation of customized wavelets for the analysis of γ-ray spectra." *Nuclear Instruments and Methods in Physics Research Section A: Accelerators, Spectrometers, Detectors and Associated Equipment*, vol. 579, No. 1 (Apr. 24, 2007), pp. 275-278.

Burr, T., and Myers, K. "Signatures for several types of naturally occurring radioactive materials." *Applied Radiation and Isotopes*, vol. 66, No. 9 (2008), pp. 1250-1261.

Sonego, P., Kocsor, A., and Pongor, S. "ROC analysis: applications to the classification of biological sequences and 3D structures." *Briefings in bioinformatics*, vol. 9, No. 3 (2008), pp. 198-209.

Committee on Advanced Spectroscopic Portals, National Research Council, *Evaluating Testing, Costs, and Benefits of Advanced Spectroscopic Portals for Screening Cargo at Ports of Entry*. Interim Report (Abbreviated Version), 2009, 91 pages.

Estep, R. J., and Mayo, D. R. "Application of the multiple isotope material basis set (MIMBS) method of isotope identification to low energy gamma emitters." *Journal of Radioanalytical and Nuclear Chemistry*, vol. 282, No. 3 (2009), pp. 877-881.

Runkle, R. C., Smith, L. E., and Peurrung, A. J. "The photon haystack and emerging radiation detection technology." *Journal of Applied Physics*, vol. 106, No. 4 (2009), 041101, 21 pages.

Notice of Acceptance dated Feb. 11, 2015 in AU Patent Application No. 2012283743, 2 pages.

European Search Report dated Mar. 20, 2015 in EP Patent Application No. 12810784.4, 5 pages.

Notice of Reasons for Rejection dated Apr. 25, 2016, from JP Application No. 2014-517342, (6 pages).

Office Action dated Aug. 7, 2018 in KR 10-2014-7000942, 5 pages.

European Search Report dated May 22, 2019 in EP Patent Application No. 12810784.4, 4 pages.

Tao Li et al., "Using discriminant analysis for multi-class classification: an experimental investigation", Knowledge and Information Systems (2006) 10(4): 453-472, DOI 10.1007/s10115-006-0013-y, London, 20 pages.

* cited by examiner

RADIONUCLIDE DETECTION AND IDENTIFICATION

CROSS-REFERENCES TO RELATED APPLICATIONS

This application is a National Stage of International Application No. PCT/AU2012/000818, filed Jul. 6, 2012, and which claims the benefit of Australian Patent Application No. 2011902731, filed Jul. 8, 2011, the disclosures of which are incorporated herein by reference.

FIELD

The present invention relates to detecting and identifying radioactive materials, and in particular to processing gamma ray spectra for this purpose.

PRIORITY CLAIM

The present application claims priority from Australian Provisional Application No. 2011902731, the entire contents of which are incorporated herein by cross-reference.

BACKGROUND

There are many applications that require detecting the presence of, and if possible identifying, radioactive materials in target objects or regions. One such application is to prevent unauthorised passage of certain such materials across borders into nations or regions where such materials are prohibited. A suitable method in this border-monitoring application would be capable of performing the detection/identification as a vehicle passed through a detection zone, preferably without stopping in the zone, so as not to excessively impede the flow of traffic. Thus the method would preferably be capable of detecting the presence of prohibited materials rapidly, for example in a period of about 10 seconds or less. The method should preferably have high sensitivity, i.e. a low level of false negatives (failing to detect the presence of prohibited material) and high specificity, i.e. low false positives (signalling a detection when no prohibited material is present).

Detection of prohibited radionuclides is complicated by the fact that non-prohibited radionuclides, like prohibited radionuclides, may emit a certain level of ionising radiation, for example due to the presence of elevated concentrations of naturally occurring radioactive materials (NORMs), or of legitimate radiopharmaceutical products etc. Some existing systems, which use simple plastic scintillation detectors, measure only the gross level of radiation, in the form of gamma rays, emitted by a target. Such systems are prone to a high rate of nuisance alarms if the threshold level of radiation detection is set too low or a high rate of false negatives if the threshold level of radiation detection is set too high. Also, such systems are unable to distinguish legitimately traded goods containing elevated concentrations of NORMs from illicit or inadvertent and unlicensed goods containing prohibited radioactive materials.

A second generation of systems, known as Spectroscopic Portal Monitors (SPMs), based on NaI and HPGe detectors, seek to acquire the gamma ray spectrum of the target. Such systems contain processing to compare the acquired gamma ray spectrum with the spectra of radionuclides of interest. The spectrum processing methods have included, but not been limited to, those based on peak detection and matching, artificial neural networks, response function fitting, template matching, and wavelets.

High resolution spectroscopic equipment of the type found in SPMs is very expensive and is subject to poor reliability in field deployment due to the challenging operating conditions. Lower resolution spectroscopic equipment is less expensive and more robust but yields poorer performance with respect to radionuclide detection, namely higher rates of both false positives and false negatives.

SUMMARY OF INVENTION

It is an object of the present invention to substantially overcome, or at least ameliorate, one or more disadvantages of existing arrangements.

According to a first aspect of the invention there is provided a method of processing a gamma ray spectrum acquired from a target, the method comprising: determining whether the gamma ray spectrum of the target belongs to a first class of a plurality of classes, the first class containing reference gamma ray spectra of one or more radionuclide sources of interest, using optimal loading coefficients associated with the one or more radionuclide sources of interest, wherein the optimal loading coefficients have been obtained using Fisher linear discriminant analysis; and generating an output signal dependent on the determining. In this context, a "class" is taken to refer to a set of gamma ray spectra with a common property, such as being gamma ray spectra of one or more radionuclide sources of interest. "Sources of interest" includes the "null" source referred to herein as "background". "Reference" gamma ray spectra are gamma ray spectra that belong to a set or "library" of previously acquired spectra. A class may contain reference gamma ray spectra as well as other gamma ray spectra, such as the gamma ray spectrum acquired from the target. In this context, a "plurality" of classes is taken to refer to two or more classes, for example two, three, four . . . .

The following options may be used in conjunction with the first aspect, either individually or in any suitable combination.

The optimal loading coefficients may be obtained using Fisher linear discriminant analysis comprising: computing a between-class scatter matrix and a within-class scatter matrix for the reference gamma ray spectra in each class; and computing the optimal loading coefficients from the generalised eigenvector corresponding to the largest generalised eigenvalue of the between-class and within-class scatter matrices.

The optimal loading coefficients may alternatively be obtained using Fisher linear discriminant analysis comprising: allocating reference gamma ray spectra from a training data library among at least two classes, such that reference gamma ray spectra corresponding to the one or more radionuclide sources of interest are allocated to a first class; computing a between-class scatter matrix and a within-class scatter matrix for the reference gamma ray spectra in each class; and computing the optimal loading coefficients from the generalised eigenvector corresponding to the largest generalised eigenvalue of the between-class and within-class scatter matrices.

The step of determining whether the gamma ray spectrum of the target belongs to the first class may be carried out within a region of interest of the gamma ray spectra belonging to the first class.

The step of determining whether the gamma ray spectrum of the target belongs to the first class may comprise computing a distance between the gamma ray spectrum of the target projected by the optimal loading coefficients and a second class containing further gamma ray spectra of further radionuclide sources projected by the optimal loading coefficients; and determining whether the gamma ray spectrum of the target belongs to the first class using the computed distance.

The determining may comprise determining whether the computed distance is above a threshold distance.

The computed distance may be a Mahalanobis distance. The computed distance may be a Euclidean distance.

The method according to the first aspect may further comprise determining the threshold distance using the steps of: determining the mean gross counts in the second class; estimating the standard deviation of the second class using a power law relationship with the mean gross counts; and determining the threshold distance as a predetermined number of standard deviations of the second class.

The method according to the first aspect may further comprise, if the gamma ray spectrum of the target is determined to belong to the first class, estimating the intensity of the one or more radionuclide sources of interest in the target based on the computed distance.

The method according to the first aspect may further comprise pre-processing the gamma ray spectrum of the target before determining whether the gamma ray spectrum of the target belongs to the first class. The pre-processing may comprise one or more of the following: intensity normalisation; and spectrum standardisation.

The method according to the first aspect may further comprise pre-processing the reference gamma ray spectra in each class before computing the scatter matrices. The pre-processing may comprise one or more of the following: intensity normalisation; and spectrum standardisation.

The step of generating may comprise generating the output signal if the gamma ray spectrum of the target is determined to belong to the first class.

The reference gamma ray spectra in the first class may be reference spectra of only one radionuclide source of interest. The reference gamma ray spectra in the second class may be reference spectra only of radionuclide sources of interest other than the one radionuclide source of interest.

The method may further comprise repeating the determining and generating for each of a set of radionuclide sources of interest.

The classes may be defined by a user. One user-defined class may contain at least one artificial gamma ray spectrum.

The number of classes may be greater than two. The reference gamma ray spectra in each class may be reference spectra of only one unique radionuclide source of interest.

The method according to the first aspect may further comprise activating an alarm in response to the generated output signal.

The method according to the first aspect may further comprise acquiring the gamma ray spectrum of the target as the target passes through a detection zone. The acquiring may be performed without the target stopping in the detection zone. The gamma ray spectrum of the target may be acquired in less than about 10 seconds. It may be acquired by means of a portable gamma ray detector.

In an embodiment, there is provided a method of processing a gamma ray spectrum acquired from a target, the method comprising: obtaining optimal loading coefficients associated with the one or more radionuclide sources of interest using Fisher linear discriminant analysis; determining whether the gamma ray spectrum of the target belongs to a first class of a plurality of classes, the first class containing reference gamma ray spectra of the one or more radionuclide sources of interest, using the optimal loading coefficients; and generating an output signal dependent on the determining. In this embodiment the obtaining may comprise the steps of: computing a between-class scatter matrix and a within-class scatter matrix for the reference gamma ray spectra in each class; and computing the optimal loading coefficients from the generalised eigenvector corresponding to the largest generalised eigenvalue of the between-class and within-class scatter matrices, wherein the determining whether the gamma ray spectrum of the target belongs to the first class comprises computing a distance between the gamma ray spectrum of the target projected by the optimal loading coefficients and a second class containing further gamma ray spectra of further radionuclide sources projected by the optimal loading coefficients; and determining whether the gamma ray spectrum of the target belongs to the first class using the computed distance, wherein the determining comprises determining whether the computed distance is above a threshold distance which is determined by the steps of: determining the mean gross counts in the second class; estimating the standard deviation of the second class using a power law relationship with the mean gross counts; and determining the threshold distance as a predetermined number of standard deviations of the second class.

According to a second aspect of the invention, there is provided an apparatus comprising: a gamma ray detector configured to acquire a gamma ray signal from a target; a multichannel analyser configured to partition the acquired gamma ray signal into energy bins, thereby generating a gamma ray spectrum; a memory configured to store the generated gamma ray spectrum, and a processor configured to execute computer program code to cause the processor to perform a method of processing the gamma ray spectrum of the target, the computer code comprising: code for determining whether the gamma ray spectrum of the target belongs to a first class of a plurality of classes, the first class containing reference gamma ray spectra of one or more radionuclide sources of interest, using optimal loading coefficients associated with the one or more radionuclide sources of interest, wherein the optimal loading coefficients have been obtained using Fisher linear discriminant analysis; and code for generating an output signal dependent on the determining.

The apparatus may be suitable for, or adapted for, performing the method of the first aspect. The method of the first aspect may be conducted using the apparatus of the second aspect.

According to a third aspect of the invention, there is provided a computer program code executable by a computer apparatus to cause the computer apparatus to execute a method of processing a gamma ray spectrum acquired from a target, said code comprising: code for determining whether the gamma ray spectrum of the target belongs to a first class of a plurality of classes, the first class containing reference gamma ray spectra of one or more radionuclide sources of interest, using optimal loading coefficients associated with the one or more radionuclide sources of interest, wherein the optimal loading coefficients have been obtained using Fisher linear discriminant analysis; and code for generating an output signal dependent on the determining.

The computer program code may be suitable for use in the method of the first aspect. It may be adapted for use in the apparatus of the second aspect.

According to a fourth aspect of the invention, there is provided a computer readable storage medium having a computer program recorded thereon, the program being executable by a computer apparatus to cause the computer apparatus to execute a method of processing a gamma ray spectrum acquired from a target, said code comprising: code for determining whether the gamma ray spectrum of the target belongs to a first class of a plurality of classes, the first class containing reference gamma ray spectra of one or more radionuclide sources of interest, using optimal loading coefficients associated with the one or more radionuclide sources of interest, wherein the optimal loading coefficients have been obtained using Fisher linear discriminant analysis; and code for generating an output signal dependent on the determining.

The computer readable storage medium may be the memory of the apparatus of the second aspect. The computer program recorded thereon may be the computer code of the apparatus of the second aspect. The computer program recorded thereon may be the computer code of the third aspect.

BRIEF DESCRIPTION OF DRAWINGS

One or more embodiments of the present invention will now be described, by way of an example only, with reference to the accompanying drawings wherein:

FIGS. 3a and 3b form a schematic block diagram of a general purpose computer system which may be used as the computing system in the apparatus of FIG. 1 or 1a.

DESCRIPTION OF EMBODIMENTS

The present disclosure is related to an earlier PCT application, numbered PCT/AU2010/001509, made by the present applicant and entitled "Anomaly detection of radiological signatures", the entire content of which is incorporated herein by reference.

The presently disclosed approach to radionuclide detection and identification is to acquire reference gamma ray spectra of radionuclide sources and to compare an acquired gamma ray spectrum of the target (the target spectrum) with the reference spectra. If the target spectrum is determined to belong to a first class containing the reference gamma ray spectra of a radionuclide source of interest, the target is deemed to contain the radionuclide source of interest. The disclosed approach uses Fisher Linear Discriminant Analysis (FLDA) to determine whether the target spectrum belongs to the first class containing the reference gamma ray spectra of the radionuclide source of interest. Further, it enables this determination to be made rapidly, for example as the target is passing through a checkpoint. This enables rapid decisions to be made as to whether the target is acceptable and, for example, whether it should be permitted to pass through the checkpoint. Approaches employing principal component analysis (PCA) produce loading coefficients ordered in terms of the highest variance in the data. Although the first few loading coefficients may explain a large proportion of the variation in the data, they may not represent the optimised separation between classes. The benefit of the FLDA technique is that it allows the determination of optimised loading coefficients, which maximise the separation between classes.

One feature of the disclosed approach is that each target spectrum may be pre-processed by functions that manipulate the spectrum in order to improve the classification performance. These functions may include, but not be limited to, intensity normalisation and spectrum standardisation.

The disclosed approach may include calibrating the device used for acquiring the gamma ray spectra. Over time the photopeaks of the spectra may drift, and calibration restores the correct energy values of the photopeaks. Calibration may be applied to the target gamma ray spectrum and/or to the reference gamma ray spectra. Calibration, either of the target gamma ray spectrum or of the reference gamma ray spectra, or of both, may be for the purpose of standardising the device used for acquiring the gamma ray spectra. Calibration may be conducted on a regular basis, for example, each time a spectrum is acquired, or every 5 spectra, or every 10, 15, 20, 25, 30, 35, 40, 45 or 50 spectra. Alternatively, calibration may be conducted at regular time intervals, for example every hour, or every 2, 3, 4, 5, 6, 12, 24 or 48 hours.

A gamma ray spectrum may be acquired by a gamma ray detector. This may for example be a thallium-doped sodium iodide (NaI(Tl))-based gamma ray detector. The gamma ray detector may alternatively be based on other materials such as High Purity Germanium (HPGe), Cadmium Telluride (CdTe), Cadmium Zinc Telluride (CZT) and Lanthanum Bromide (LaBr). A NaI(Tl)-based detector may be used in a thallium-doped sodium iodide based spectroscopic radiation portal monitor (RPM) in a border-monitoring application. The NaI(Tl) based detector may be used in a handheld configuration, backpack configuration or some other portable configuration of the disclosed radionuclide detection system. The raw acquired gamma ray signals (either of the target or of reference samples) may be passed to a signal amplifier for amplifying the signals. The (amplified) gamma ray signals (either of the target or of reference samples) may be passed to a multichannel analyser, which divides the signals into a number of bins (or energy ranges). The bin values are collectively referred to as a spectrum. The bins represent the smallest increment of energy interval of the gamma ray spectrum to which counts are attributed. Typically the multichannel analyser will generate values in about 1024 data bins, although there may be more or fewer than this number depending on the analyser, for example between 128 and 16384 bins, between 128 and 512 bins, between 512 and 2048 bins, between 2048 and 8192 bins, between 8192 and 16384 bins, between 512 and 4096 bins, or between 256 and 8192 bins. The number of bins is advantageously equal to an integral power of two. Typically, the bins cover energy values in the range 40 keV to 3000 keV, although these endpoints may be greater or lesser depending on the analyser, for example 30 keV and 2700 keV respectively. The range may be one of 30 keV to 2700 keV, 35 keV to 2700 keV, 40 keV to 2700 keV, 30 keV to 3000 keV, 35 keV to 3000 keV, 40 keV to 3000 keV, 30 keV to 4000 keV, 35 keV to 4000 keV and 40 keV to 4000 keV.

The number of values in a spectrum may be reduced, i.e. the spectrum may be rebinned. Rebinning may improve the computational speed. In general, each interval, or bin, in the acquired spectrum has an identical width. Rebinning the spectrum may involve uniformly increasing the width of each energy bin, thereby decreasing the total number of bins over the full energy range and increasing the number of counts within the newly defined bins. However, rebinning is not necessarily limited to linear functions. The rebinned spectrum may contain non-uniform bin widths which may, for example, be proportional to the energy squared or to some other suitable function of energy. The energy bins at higher energies may be larger than the lower energy bins, in order to ensure that the higher energy bins have sufficient counts. The rebinned spectrum may also contain user-defined bin widths, which may vary over the energy range. The number of energy bins of the rebinned spectrum is the number of variables in each spectrum. The greater the number of variables in a spectrum, the greater the computational time of the processing method. The spectra may be rebinned according to different functions. This may enable spectra from different detectors (of the same type, e.g. NaI-based) to be combined. The rebinning of the reference spectra and the target spectrum may be such that all spectra use the same energy bins.

As mentioned above, the (rebinned) target spectrum may be pre-processed. Pre-processing may involve either or both of intensity normalisation and spectrum standardisation.

For intensity normalisation, a target spectrum is normalised by the value in the energy bin with the highest number of counts. Intensity normalisation removes the effects of the wide range of detector acquisition times, which can occur for example at ports of entry in a border monitoring application, and the effect of variation of the speed of passage of a target through the detection zone of an RPM in a border monitoring application.

For spectrum standardisation, a target spectrum is translated and scaled to have zero mean and unit variance across all energy bins.

A training data library comprises reference gamma ray spectra which are acquired from known samples of radionuclide sources of interest. These sources may be naturally occurring radioactive materials (NORMs), or man-made radionuclides that are known to be benign (acceptable), or represent a threat (unacceptable). The reference spectra may also comprise mixtures of such radionuclides, shielded or masked radionuclides, and combinations thereof that represent a threat.

The reference gamma ray spectra in the training data library may have been pre-processed in a similar fashion to the target spectra. This may provide more meaningful comparisons with the target spectra.

The disclosed approach enables a relatively rapid determination of whether a target contains a particular radionuclide. In a border monitoring application, the target may be, or may be transported by, a person, a truck or a car or a train carriage or some other vehicle or part thereof. Thus if the disclosed method determines that the target contains the particular radionuclide, an output signal may be generated. If that radionuclide is anomalous (of concern), an alarm may be activated. In some cases it may be useful to generate an output signal indicating that the target does not contain the particular radionuclide in the event that the method so determines. In some cases the generated output may indicate which of a group of radionuclides is present in the target. A suitable alarm may be activated in response to the presence of a particular radionuclide of interest, for example an audible alarm (e.g. a horn, siren or similar), a visual alarm (e.g. a light, optionally a flashing light), activation of a barrier (e.g. lowering a boom gate, raising road spikes, closing a gate) to prevent passage of the target, activation of an instruction to a driver of the target (e.g. illumination of a STOP sign, activation of audible instructions to said driver) or some other type of alarm. The generated signal may also be a logic state provided to another system for the purpose of recognising the signal and responding. More than one of these types of alarm may be activated. They may be activated simultaneously. They may be activated non-simultaneously. They may be activated sequentially. Thus the disclosed apparatus may comprise one or more of an audible alarm device, a visual alarm device and a physical alarm device such as an activatable barrier. The disclosed method correspondingly may comprise activating the activatable barrier when a target is identified as an anomalous radionuclide.

An alternative mode of operation is for a signal to be generated only when the target does not contain an anomalous radionuclide (i.e. only for normal or acceptable radionuclides). In this case an activatable barrier may be removed or retracted in response to the signal, allowing a vehicle carrying no anomalous materials to pass.

Figure 1:
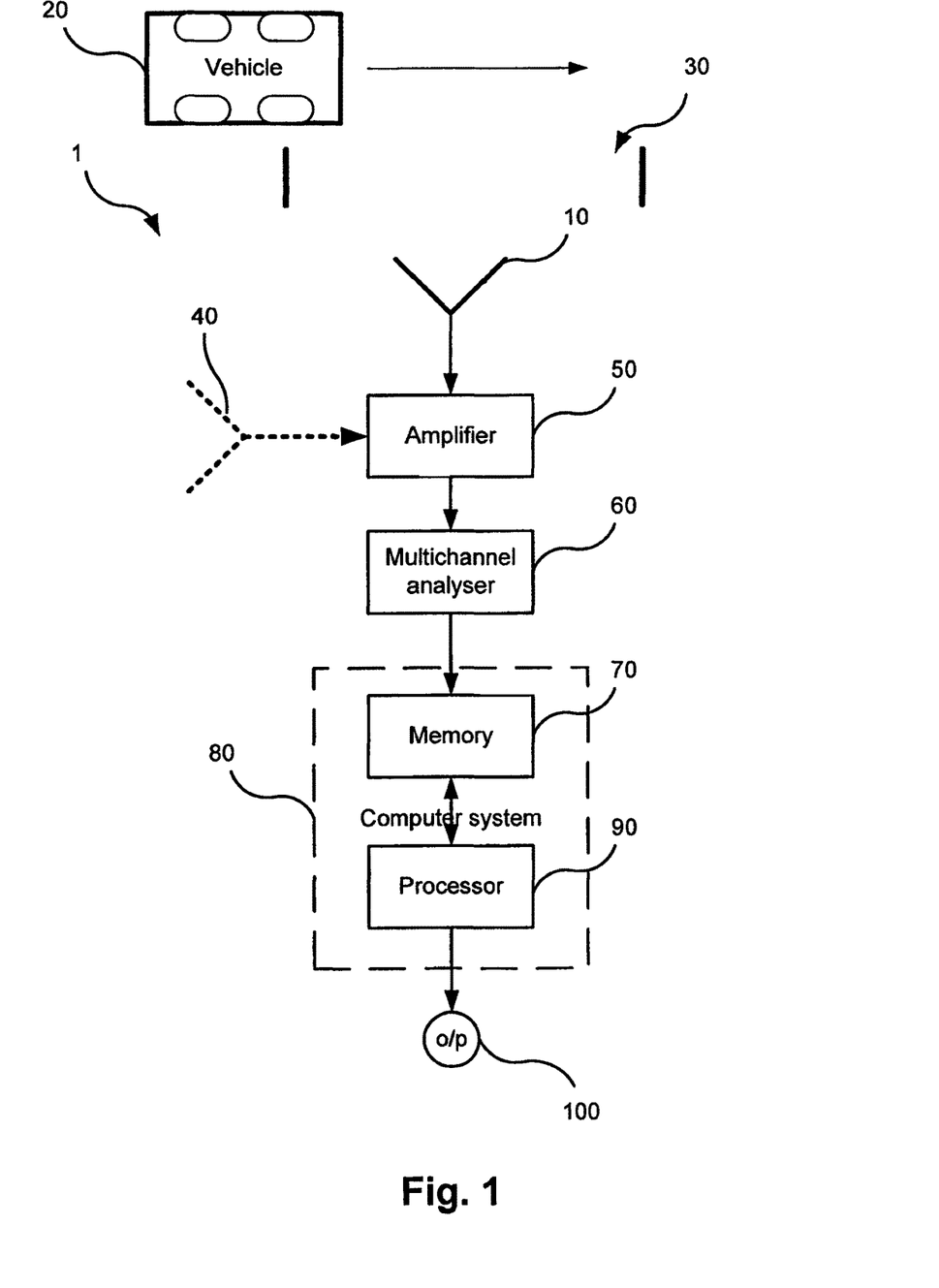
FIG. 1 is a block diagram of an apparatus within which embodiments of the invention may be practised.

FIG. 1 is a block diagram of an apparatus 1 within which embodiments of the present invention may be practised. The detector 10 is a spectroscopic portal detector, e.g. a NaI(Tl) based detector, deployed to acquire a gamma ray spectrum from a target, e.g. a vehicle 20 passing through a detection zone 30. The apparatus 1 may also comprise a reference detector 40 for acquiring reference spectra, although this may in some embodiments be omitted. In such embodiments, the main detector (detector 10) is capable of acquiring both the reference spectra and the target spectra. For example, "background" reference spectra may be acquired when no target is within the detection zone 30. If a reference detector 40 is used, it may be remote from the portal detector 10. The reference detector 40, if present, may be shielded from the detection zone 30.

An amplifier 50 is coupled to detector 10 for amplifying data from detector 10, and, if present, reference detector 40. Amplifier 50 is in turn coupled to a multichannel analyser 60 for providing an initial binning of the amplified data from amplifier 50. Multichannel analyser 60 is coupled to the memory 70 of computer system 80 so that spectra from the analyser 60 may be stored in the memory 70. Memory 70 also contains a training data library of reference spectra. Memory 70 is coupled to a processor 90, also part of the computer system 80, for processing the data stored in the memory 70 in order to determine if the target contains a given radionuclide source. An output signal 100 is generated if the target 20 is determined to contain one or more anomalous radionuclides. The output signal 100 is a logic state provided to another system (not shown) that is configured to recognise the output signal 100 and take appropriate action, such as activating an alarm. The alarm may take one or more of the following forms, simultaneously or sequentially: visual output, (e.g. a light, optionally a flashing light, or illumination of a STOP sign); audible output, (e.g. a horn, siren or similar, or verbal instructions to the driver).

Figure 1A:
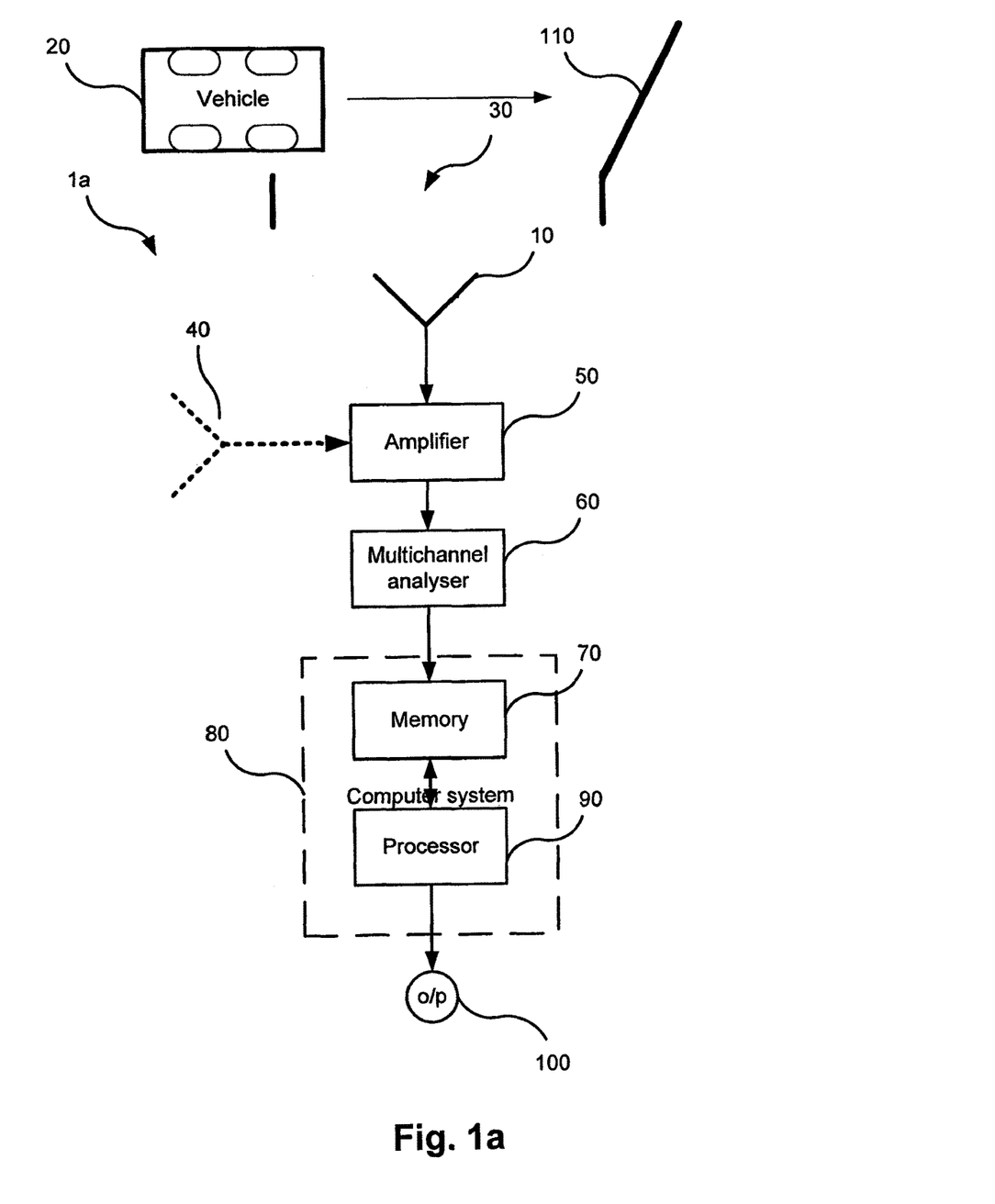
FIG. 1a is a block diagram of an alternative apparatus within which embodiments of the invention may be practised.

FIG. 1a is a block diagram of an alternative apparatus 1a within which the embodiments of the invention may be practised. The apparatus 1a is similar to the apparatus 1 of FIG. 1, with the addition of an activatable barrier 110 that is able to prevent passage of vehicle 20 in the event that the target is determined to contain one or more anomalous radionuclides. The activatable barrier 110 is in a normally open state (i.e. in a state in which passage of the vehicle 20 is allowed), and activating the barrier 110 closes the barrier 110 so as to hinder or prevent passage of the vehicle 20. In the apparatus 1a, the output signal 100 causes the barrier 110 to be activated to prevent passage of vehicle 20 through the detection zone 30. The activation of the barrier 110 could take one or more of the following forms: lowering a boom gate; raising road spikes; closing a gate.

In operation, vehicle 20 passes through detection zone 30. This typically does not involve vehicle 20 stopping its forward motion, and commonly takes about 5 to about 80 seconds. Detector 10 acquires gamma ray photons from vehicle 20 during this period and generates a resulting signal that is passed to amplifier 50, which amplifies the signal. The amplified signal is then passed to multichannel analyser 60 which performs an initial binning of the amplified target signal and passes a binned target spectrum to memory 70 for storage. Detector 10 may also be used for acquiring reference spectra for use in creating the training data library. In any event, the reference spectra are pre-processed as described above for the target spectrum, and then stored in memory 70.

Pre-processed spectra stored in memory 70 are processed by processor 90 as described below in order to obtain a decision criterion. Processor 90 then determines from this decision criterion whether the target contains an anomalous radionuclide and, if so, generates an output signal 100. Appropriate action may then be taken in response to the output signal 100, for example vehicle 20 may be diverted for further investigation, an alarm may be activated, or in the apparatus 1a of FIG. 1a, the activatable barrier 110 may be activated so as to prevent passage of vehicle 20.

As mentioned above, an alternative mode of operation of the apparatus 1 or 1a is to generate the output signal 100 only when the target is determined not to contain an anomalous radionuclide. In this mode of operation, the activatable barrier 110 would normally be in a closed state (i.e. in a state in which passage of the vehicle 20 is prevented or hindered), and activating the barrier 110 opens the barrier so as to allow or facilitate passage of the vehicle 20. The barrier 110 would be activated in response to the output signal 100, allowing a vehicle 20 carrying no anomalous radionuclides to pass. Thus the operation of the apparatus 1a may comprise generating the output signal 100 to the barrier 110 which prevents or hinders passage of the vehicle 20 when the vehicle 20 is identified as containing anomalous radionuclides and which allows passage of the vehicle 20 when the vehicle 20 is identified as not containing an anomalous radionuclide.

The apparatus 1 may also comprise a camera or similar photographic recording device (not shown). Such a device may be used for recording images of all vehicles passing through the detection zone, or for recording images of vehicles passing through the detection zone only when an anomalous radionuclide source is detected. The camera may be used for transmitting to an operator an image of all vehicles passing through the detection zone, or for transmitting to said operator images of vehicles passing through the detection zone only when an anomalous source is detected. In this case, the signal from the camera may be transmitted to a video display for displaying the image(s) to the operator. The disclosed method may comprise detecting, and recording and/or transmitting, an image of the vehicle or of a part (e.g. a number plate thereof), either for each vehicle passing through the detection zone or for each vehicle passing through the detection zone which is identified as an anomalous source or as containing an anomalous source.

In acquiring the target gamma ray spectrum, the vehicle 20 passes through a detection zone 30, over which the detector 10 is capable of acquiring the gamma ray spectrum. The vehicle 20 may pass through the detection zone 30 at a mean velocity of about 1 to about 12 km/h, or about 1 to 8, 1 to 5, 5 to 10, 1 to 3, 3 to 5 or 2 to 4 km/h, e.g. about 1, 1.5, 2, 2.5, 3, 3.5, 4, 4.5, 5, 6, 7, 8, 9, 10, 11 or 12 km/h. The time for passage of the vehicle 20 through the detection zone 30 may be about 5 to about 80 seconds, or about 5 to 50, 5 to 20, 5 to 15, 10 to 80, 50 to 80, 20 to 50 or 5, 5 to 15, 15 to 20, 5 to 10, 10 to 15 or 7 to 12 seconds, e.g. about 5, 6, 7, 8, 9, 10, 11, 12, 13, 14, 15, 20, 25, 30, 35, 40, 45, 50, 55, 60, 65, 70, 75 or 80 seconds. The detection zone may be about 5 to about 25 meters long, or about 5 to 20, 5 to 15, 5 to 10, 10 to 25, 15 to 25 or 10 to 10 meters, e.g. about 5, 10, 15, 20 or 25 meters. The vehicle 20 may be a truck or a car or a train carriage or some other vehicle or part thereof.

The processing method carried out by the processor 90 of the computing system 80 makes use of Fisher Linear Discriminant Analysis (FLDA). For a set of N observations ($x_1, x_2, \ldots x_N$), each observation being a vector of length n, and for a two-class problem where each observation belongs to one of two classes $c_0$ and $c_1$, FLDA is formulated as follows.

The means of the two classes are labelled as $\mu_0$ and $\mu_1$ and the class covariances as $\Sigma_0$ and $\Sigma_1$. The within-class scatter matrix $S_W$ is defined as $$S_W = \sum_{i=0}^{1} \sum_{x_k \in c_i} (x_k - \mu_i)(x_k - \mu_i)^T \qquad \text{Equation 1}$$

while the between-class scatter matrix $S_B$ is defined as $$S_B = \sum_{i=0}^{1} N_i (\mu_i - \mu)(\mu_i - \mu)^T \qquad \text{Equation 2}$$

where $N_1$ is the number of observations in class $c_1$ and $\mu$ is the mean of all N observations.

Projection of each observation x using an n by 1 projection vector w of "loading coefficients" transforms the means of the two classes to scalars $w^T \mu_0$ and $w^T \mu_1$. The within-class and between-class scatter matrices $S_W$ and $S_B$ are respectively transformed to scalars $w^T S_W w$ and $w^T S_B w$.

The "separation" J between the two projected classes as a function of the projection vector w is defined as the ratio of the projected between-class scatter matrix to the projected within-class scatter matrix:

$$J(w) = \frac{w^T S_B w}{w^T S_W w} \qquad \text{Equation 3}$$

According to FLDA, the "optimal" projection vector $w_{opt}$ is the projection vector that maximises the separation J between the two projected classes. It may be shown that the optimal projection vector $w_{opt}$ is the generalised eigenvector of $S_B$ and $S_W$ corresponding to the largest (non-infinite) generalised eigenvalue $\lambda$ of $S_B$ and $S_W$. Provided $S_W$ is non-singular, this is equivalent to finding the eigenvector of $S_W^{-1} S_B$ corresponding to the largest (non-infinite) eigenvalue $\lambda$ of $S_W^{-1} S_B$:

$$S_W^{-1} S_B w_{opt} = \lambda w_{opt} \qquad \text{Equation 4}$$

In one implementation, the following radionuclide sources are of interest: $^{241}$Am, $^{133}$Ba, $^{57}$Co, $^{60}$Co, $^{137}$Cs, Highly Enriched Uranium (HEU), $^{237}$Np, Weapons Grade Plutonium (WGPu), $^{232}$Th, 4° K, $^{226}$Ra, and Depleted Uranium (DU), and the "background". Other implementations contain many more sources of interest, or may contain fewer sources of interest. Each source of interest is known to be either benign or anomalous. The training data library contains multiple reference spectra of each of the sources of interest. The reference spectra are acquired by the gamma ray detector(s). Each reference spectrum is pre-processed before storage in the training data library as described above.

In one implementation, each of a set of sources of interest represented in the training data library is taken in turn as the current source. The reference spectra in the training data library are allocated between two classes such that reference spectra corresponding to the current source are allocated to the first class (class 0), and reference spectra corresponding to other sources are allocated to the second class (class 1). The mean $\mu_i$ and covariance $\Sigma_i$ of each class is determined, as are the within-class and between-class scatter matrices. Equation 4 is then used to determine the optimal projection vector $w_{opt}$ that maximises the separation J between the two projected classes. The determined optimal projection vector $w_{opt}$ is then stored in association with the current source.

To determine whether a target spectrum belongs in class 0 (the current source of interest) or class 1 (not the current source of interest), the pre-processed target spectrum x is projected by the optimal projection vector $w_{opt}$ associated with the current source of interest to obtain a projected target spectrum $w^T_{opt}x$. A distance between the projected target spectrum and the projected class 1 is then computed. If the distance is greater than a threshold distance, the target spectrum is determined to belong to class 0, and the target is deemed to contain a sample of the current source of interest. Otherwise, the target spectrum is determined to belong to class 1.

After all the sources of interest have been considered, the output signal 100 is generated depending on whether the target was deemed to contain at least one anomalous source of interest.

Figure 2A:
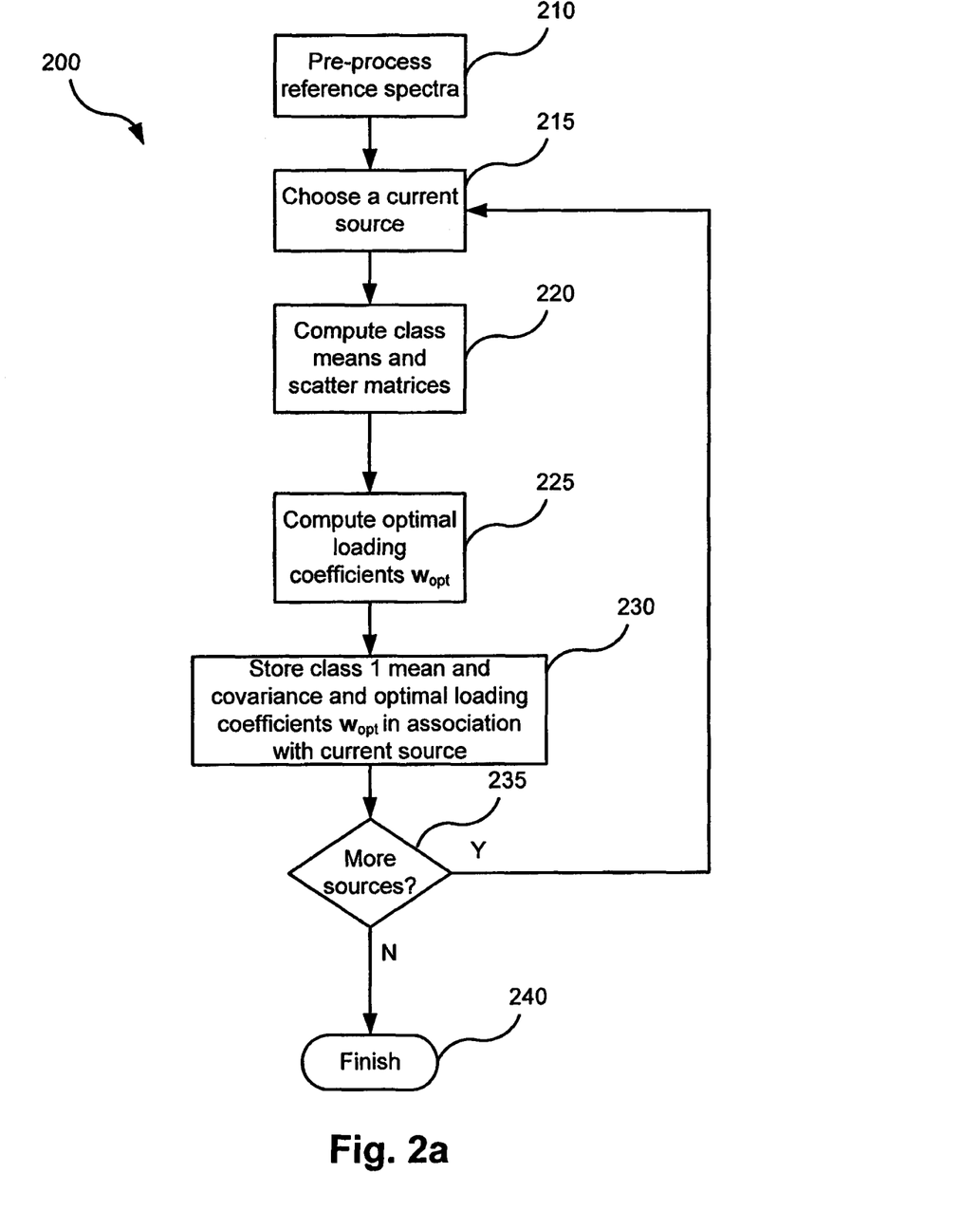
FIG. 2a is a flow chart illustrating a method of processing a training data library of reference spectra within the apparatus of FIG. 1 according to one embodiment of the invention.

FIG. 2a is a flow chart illustrating a method 200 of processing a training data library of reference spectra according to one embodiment of the invention. In one implementation, the method 200 is carried once before processing any acquired target spectra, and is controlled in its execution by the processor 90 of the computing system 80 in concert with the memory 70, as described below.

The method 200 starts at step 210, where the processor 90 pre-processes each reference spectrum in the training data library, rebinned to 440 bins, as described above. At the following step 215, the processor 90 chooses a source from the set of sources of interest that has not yet been chosen as a current source. Two classes, one containing only reference spectra corresponding to the current source (class 0), and one containing reference spectra corresponding to all other sources (class 1) are notionally constructed. At the following step 220, the processor 90 computes the mean $\mu_i$ and covariance $\Sigma_i$ of each class, and the within-class and between-class scatter matrices $S_W$ and $S_B$. Step 225 follows, at which the processor 90 determines the optimal projection vector (also referred to herein as the optimal loading coefficients) $w_{opt}$ that maximises the separation between the two classes using Equation 4. The method 200 then proceeds to step 230, at which the processor 90 stores the determined optimal loading coefficients $w_{opt}$, and the mean $\mu_1$ and covariance $\Sigma_1$ of class 1, in association with the current source. The method 200 continues at step 235, where the processor 90 determines whether there are any sources in the set of sources of interest that have not yet been chosen. If so ("Y"), the method 200 returns to step 215. If not ("N"), the method 200 concludes at step 240.

In a variation of the method 200, the processor 90 performs the computations of steps 220 and 225 not on the whole of each reference spectrum, but on some portion of each reference spectrum known as the "region of interest". In one implementation, the region of interest is that portion of the spectrum surrounding the principal peak in the spectrum of the current source. For example, for a radionuclide with a principal peak at 662 keV, the region of interest is the range between 620 keV and 700 keV. In other implementations, the region of interest comprises multiple disjoint sections of each spectrum. At step 230 in the variation, the processor 90 stores the endpoints of the region of interest alongside the other parameters for the current source.

Figure 2B:
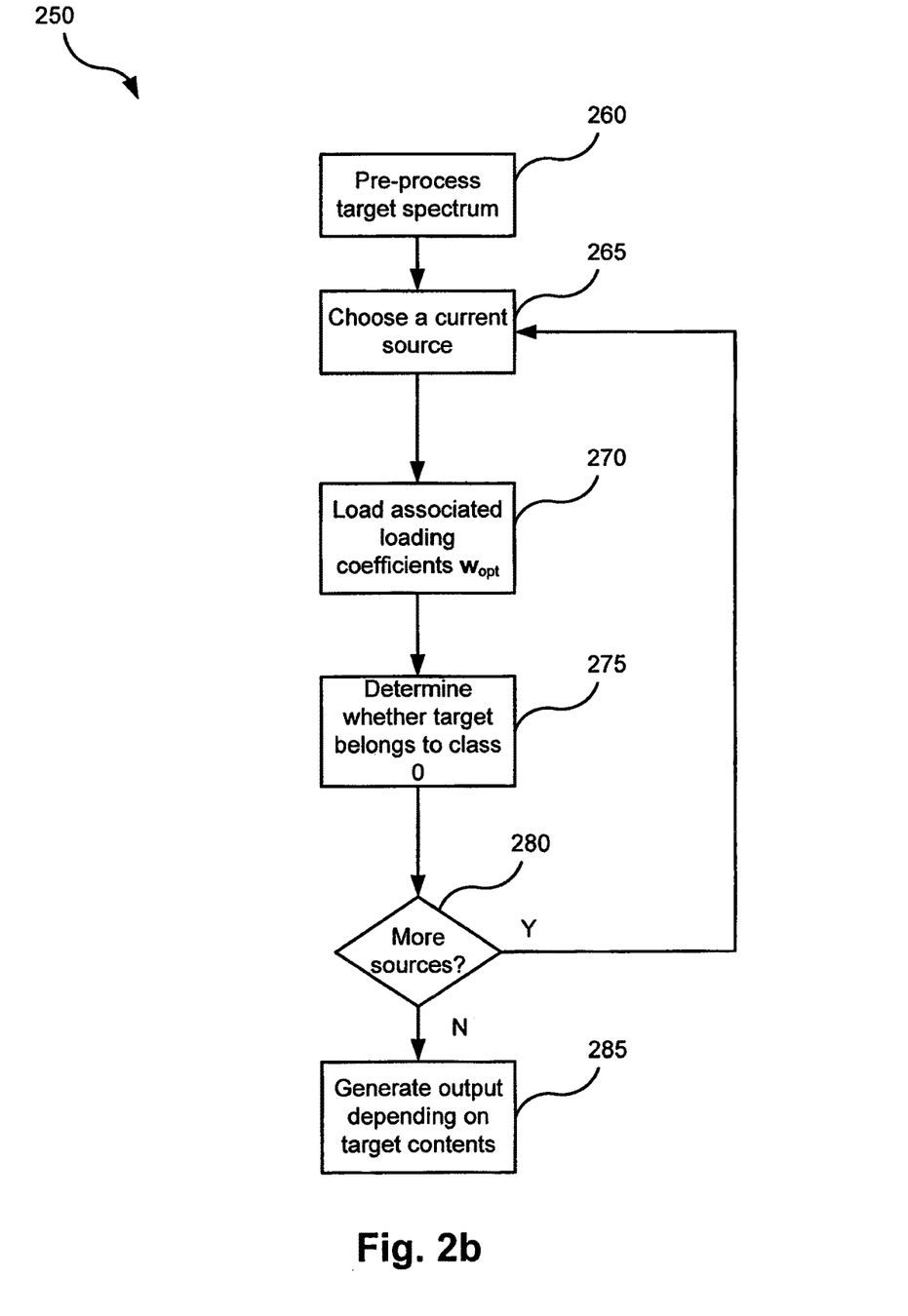
FIG. 2b is a flow chart illustrating a method of processing a target spectrum within the apparatus of FIG. 1 according to the embodiment of the invention.

FIG. 2b is a flow chart illustrating a method 250 of processing a target spectrum according to the embodiment of the invention. The method 250 is controlled in its execution by the processor 90 of the computing system 80 in concert with the memory 70, as described below.

The method 250 starts at step 260, where the processor 90 pre-processes the target spectrum, rebinned to 440 bins, as described above. At the following step 265, the processor 90 chooses a source from the set of sources of interest that has not yet been chosen as a current source. At the following step 270, the processor 90 loads the optimal loading coefficients $w_{opt}$ and the mean $\mu_i$ and covariance $\lambda_1$ of class 1 associated with the current source that were stored at step 230 of the method 200. Step 275 follows, at which the processor 90 determines whether the target spectrum belongs in class 0 (the current source of interest) or class 1 (not the current source of interest) using the optimal loading coefficients $w_{opt}$. If the target spectrum is determined to belong to class 0, the target is deemed to contain a sample of the current source.

One implementation of step 275 is for the processor 90 to compute the Mahalanobis distance D between the projected target spectrum $w^T_{opt}x$ and the projected class 1, using the mean $\mu_1$ and covariance $\Sigma_1$ of class 1 that were stored in association with the current source at step 230 of the method 200:

$$D^2=(w_{opt}^T x - w_{opt}^T \mu_1)^T (w_{opt}^T \Sigma_1 w_{opt})^{-1}(w_{opt}^T x - w_{opt}^T \mu_1) \qquad \text{Equation 5}$$

The target spectrum x is then determined to belong to class 0 if the Mahalanobis distance D is above a threshold distance from the projected class 1.

In an alternative implementation of step 275, the processor 90 computes the Euclidean distance d between the projected target spectrum $w^T_{opt}x$ and the projected class 1 using the mean $\mu_1$ of class 1:

$$d^2=(w_{opt}^T x - w_{opt}^T \mu_1)^T (w_{opt}^T x - w_{opt}^T \mu^1) \qquad \text{Equation 6}$$

The target spectrum x is then determined to belong to class 0 if the Euclidean distance d is above a threshold distance from the projected class 1.

The threshold distance used in step 275 may be obtained from the training data library or a separate set of reference spectra from class 1. In one implementation of step 275, the threshold distance is defined by a power law relationship with the mean gross counts in class 1, i.e. the mean of the sum of all counts over all bins of all reference spectra in class 1. For example, the standard deviation y of a class may be related to the mean gross counts g by the following equation:

$$y = Ag^{-B} \qquad \text{Equation 7}$$

In Equation 7, A is a positive number and B is a number between 0 and 1. For class 0, B is typically around 0.5. For class 1, B is typically between 0.4 and 0.9. In this implementation, the threshold distance is set at a number, typically between one and ten, for example five, of standard deviations of class 1. In another implementation of step 275, the threshold distance is a user defined value.

The method 250 continues at step 280, where the processor 90 determines whether there are any sources in the set of sources of interest that have not yet been chosen. If so ("Y"), the method 250 returns to step 265. If not ("N"), the processor 90 at step 285 generates the output signal 100 depending on the determined contents of the target as described above. The method 250 then concludes. The method 250 may be categorised as an "identification" method.

If the variation of the method 200 was used to process the reference spectra, then a complementary variation of the method 250 loads the endpoints of the region of interest associated with the current source at step 270 along with the optimal loading coefficients and other parameters associated with the current source, and performs the computations of step 275 within the "region of interest".

If one of the sources of interest is "background", and the method 250 does not result in an indication that the target contains any of the sources of interest, this result may be taken as an indication that the target contains a radionuclide source that is not presently in the training data library.

In an alternative embodiment, the two classes for FLDA purposes are predefined by a user. In one example, the first class comprises reference spectra corresponding to Special Nuclear Materials (fissile radionuclides) and the second class comprises reference spectra corresponding to NORMs. To process the training data library according to the alternative embodiment, the method 200 may be used, except that two classes are formed at step 215 in accordance with the user definition. Steps 220, 225, and 230 are only performed once, and step 235 is not needed. To process the target spectrum according to the alternative embodiment, the method 250 may be used, except that the steps 270 and 275 are only performed once, and there is no need for the steps 265 and 280. In the example, the result of the target spectrum processing under the alternative embodiment is a signal indicating whether a target spectrum is a Special Nuclear Material or a NORM. This alternative embodiment may be categorised as a "classification" or "anomaly detection" method.

A second example of the alternative embodiment is similar to the first example, except that the first class (corresponding to a threat) comprises at least one "artificial" gamma ray spectrum. The artificial spectrum in one implementation is a constant value with an additive Gaussian noise component. In another implementation, the artificial spectrum is a quasi-linear spectrum with an additive Gaussian noise component. The second class comprises reference spectra corresponding to NORMs. The second example has the advantage over the first example that no prior knowledge of the threat (or non-NORM) spectra is needed in order to conclude that a target contains a threat under a wide range of conditions such as different intensities or shielding materials.

Fisher linear discriminant analysis as formulated above may readily be generalised from a two-class problem to a multi-class problem. In a further example of the alternative embodiment, each class is defined to contain only reference spectra corresponding to a unique radionuclide. The number of classes can then be as many as the number of radionuclides represented in the training data library. Step 275 then returns the number of the class in which the target spectrum is determined to belong.

If the target is deemed to contain a sample of the current source of interest, the distance of the target spectrum from the projected class 1, computed in step 275 of the method 250, shows a relationship with the intensity of the current source of interest within the target that is approximately linear over small values of intensity, and tends to logarithmic over larger values of intensity. The computed distance of the target spectrum from class 1 may therefore be used in an optional processing step in the method 250 to estimate the intensity of the current source of interest within the target. The standard deviation y computed from the mean gross counts in class 1 using Equation 7 may be used to provide an error estimate for the estimated intensity of the current source of interest within the target.

Figure 3A:
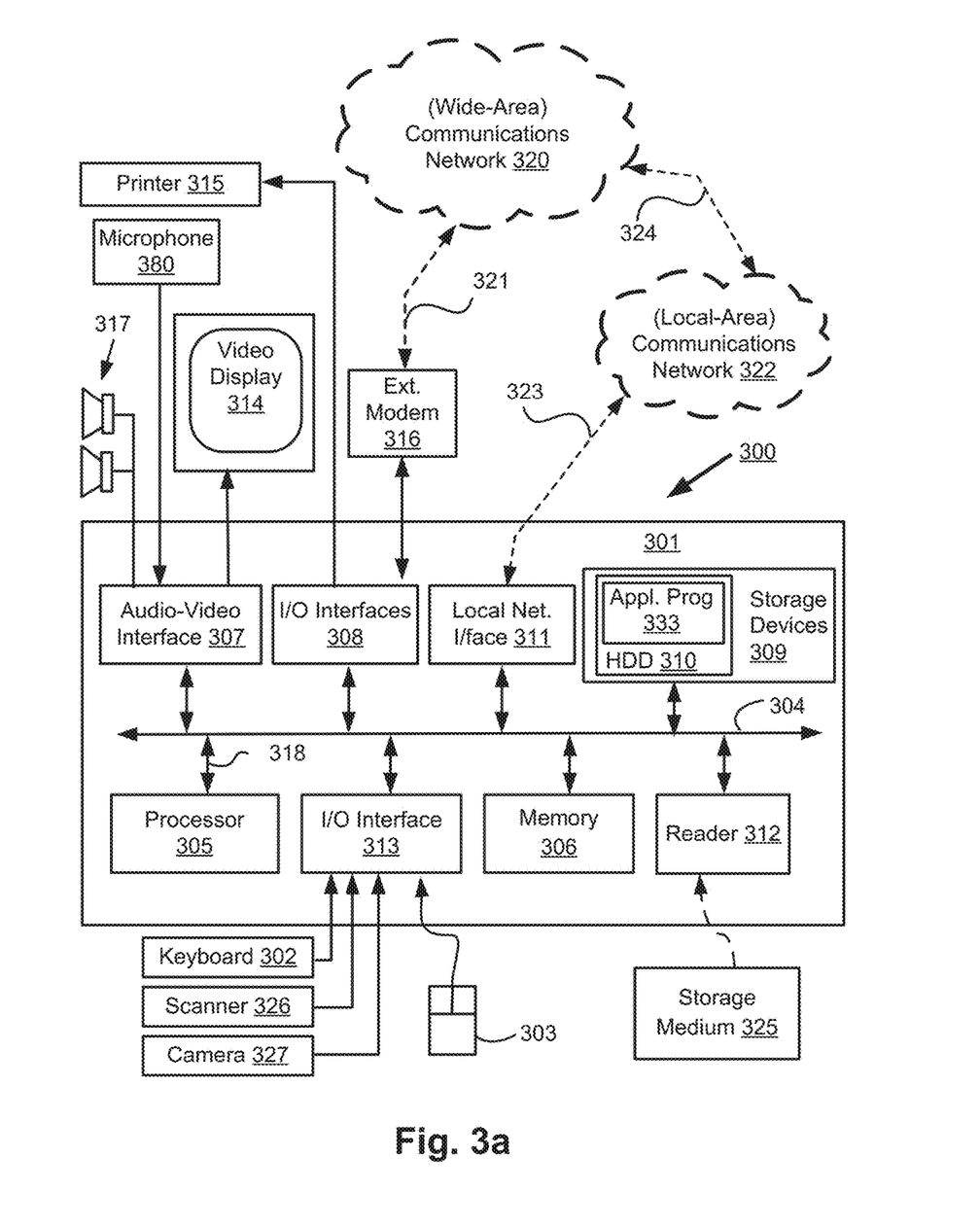
Figure 3B:
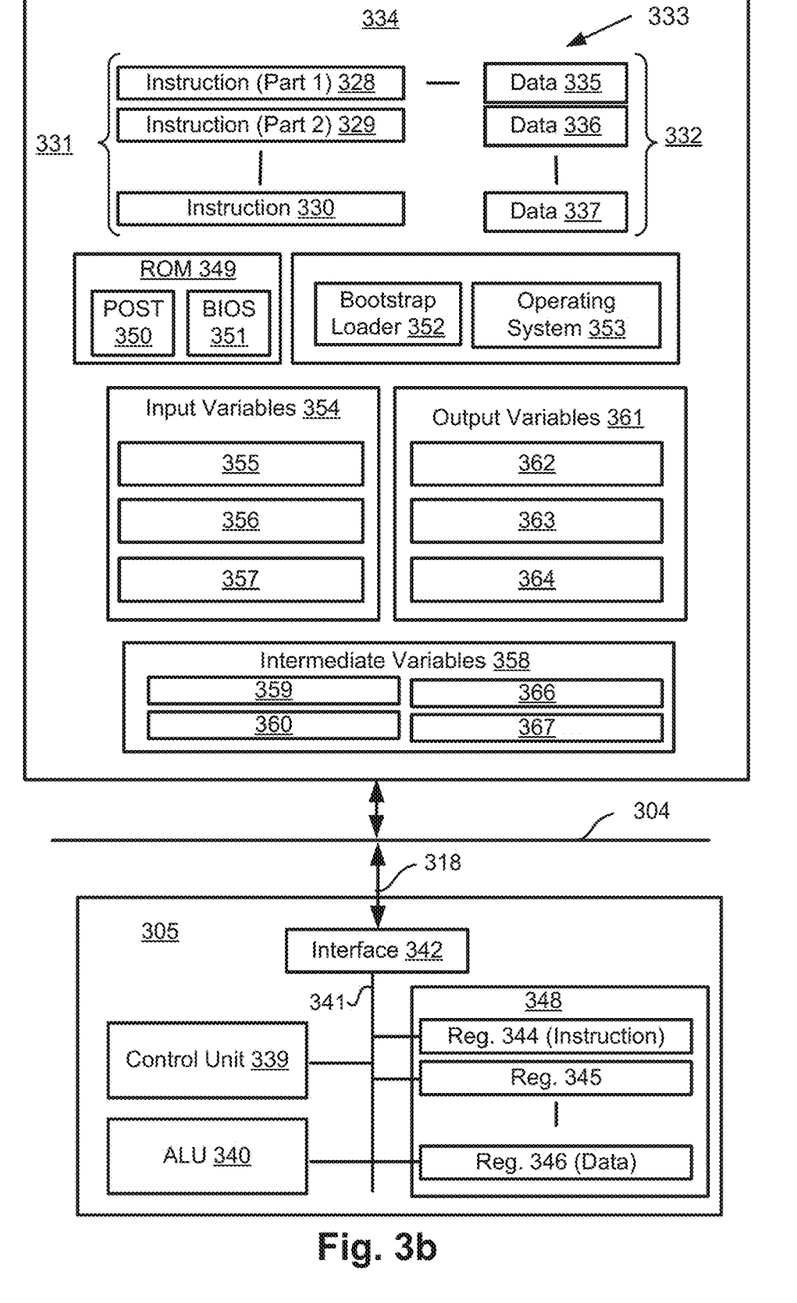

FIGS. 3a and 3b collectively form a schematic block diagram of a general purpose computer system 300, which may be used as the computing system 80 in the apparatus 1 of FIG. 1 or the apparatus 1a of FIG. 1a, to carry out the processing methods 200 and 250 of FIGS. 2a and 2b.

As seen in FIG. 3a, the computer system 300 is formed by a computer module 301, input devices such as a keyboard 302, a mouse pointer device 303, a scanner 326, a camera 327, and a microphone 380, and output devices including a printer 315, a display device 314 and loudspeakers 317. An external Modulator-Demodulator (Modem) transceiver device 316 may be used by the computer module 301 for communicating to and from a communications network 320 via a connection 321. The network 320 may be a wide-area network (WAN), such as the Internet or a private WAN. Where the connection 321 is a telephone line, the modem 316 may be a traditional "dial-up" modem. Alternatively, where the connection 321 is a high capacity (e.g. cable) connection, the modem 316 may be a broadband modem. A wireless modem may also be used for wireless connection to the network 320.

The computer module 301 typically includes at least one processor unit 305, and a memory unit 306 for example formed from semiconductor random access memory (RAM) and semiconductor read only memory (ROM). The memory unit 306 may be identified with the memory 70 of the computer system 80, and the processor unit 305 may be identified with the processor 90 of the computer system 80.

The module 301 also includes an number of input/output (I/O) interfaces including an audio-video interface 307 that couples to the video display 314, loudspeakers 317 and microphone 380, an I/O interface 313 for the keyboard 302, mouse 303, scanner 326, camera 327 and optionally a joystick (not illustrated), and an interface 308 for the external modem 316 and printer 315. In some implementations, the modem 316 may be incorporated within the computer module 301, for example within the interface 308. The computer module 301 also has a local network interface 311 which, via a connection 323, permits coupling of the computer system 300 to a local computer network 322, known as a Local Area Network (LAN). As also illustrated, the local network 322 may also couple to the wide network 320 via a connection 324, which would typically include a so-called "firewall" device or device of similar functionality. The interface 311 may be formed by an Ethernet™ circuit card, a Bluetooth™ wireless arrangement or an IEEE 802.11 wireless arrangement.

The interfaces 308 and 313 may afford either or both of serial and parallel connectivity, the former typically being implemented according to the Universal Serial Bus (USB)

standards and having corresponding USB connectors (not illustrated). Storage devices 309 are provided and typically include a hard disk drive (HDD) 310. Other storage devices such as a floppy disk drive and a magnetic tape drive (not illustrated) may also be used. An optical disk drive 312 is typically provided to act as a non-volatile source of data. Portable memory devices, such optical disks (e.g. CD-ROM, DVD), USB-RAM, and floppy disks for example may then be used as appropriate sources of data to the system 300.

The components 305 to 313 of the computer module 301 typically communicate via an interconnected bus 304 and in a manner which results in a conventional mode of operation of the computer system 300 known to those in the relevant art. Examples of computers on which the described arrangements can be practised include IBM-PC's and compatibles, Sun Sparcstations, Apple Mac™ or alike computer systems evolved therefrom.

The methods 200 and 250, described above, may be implemented as one or more software application programs 333 executable within the computer system 300. In particular, the steps of the methods 200 and 250 are effected by instructions 331 in the software 333 that are carried out within the computer system 300. The software instructions 331 may be formed as one or more code modules, each for performing one or more particular tasks. The software may also be divided into two separate parts, in which a first part and the corresponding code modules performs the methods 200 and 250 and a second part and the corresponding code modules manage a user interface between the first part and the user.

The software 333 is generally loaded into the computer system 300 from a computer readable medium, and is then typically stored in the HDD 310, as illustrated in FIG. 3a, or the memory 306, after which the software 333 can be executed by the computer system 300. In some instances, the application programs 333 may be supplied to the user encoded on one or more CD-ROM 325 and read via the corresponding drive 312 prior to storage in the memory 310 or 306. Alternatively the software 333 may be read by the computer system 300 from the networks 320 or 322 or loaded into the computer system 300 from other computer readable media. Additionally or alternatively, data, for example the training data library or reference spectra used in preparing the training data library, may be stored in the memory 310 or 306 or may be loaded into said memory from a CD or other computer readable medium, or over the internet or by some other means. Computer readable storage media refers to any non-transitory tangible storage medium that participates in providing instructions and/or data to the computer system 300 for execution and/or processing. Examples of such storage media include floppy disks, magnetic tape, CD-ROM, a hard disk drive, a ROM or integrated circuit, USB memory, a magneto-optical disk, or a computer readable card such as a PCMCIA card and the like, whether or not such devices are internal or external of the computer module 301. Examples of transitory or non-tangible computer readable transmission media that may also participate in the provision of software, application programs, instructions and/or data to the computer module 301 include radio or infra-red transmission channels as well as a network connection to another computer or networked device, and the Internet or Intranets including e-mail transmissions and information recorded on Websites and the like.

The second part of the application programs 333 and the corresponding code modules mentioned above may be executed to implement one or more graphical user interfaces (GUIs) to be rendered or otherwise represented upon the display 314. Through manipulation of typically the keyboard 302 and the mouse 303, a user of the computer system 300 and the application may manipulate the interface in a functionally adaptable manner to provide controlling commands and/or input to the applications associated with the GUI(s). Other forms of functionally adaptable user interfaces may also be implemented, such as an audio interface utilizing speech prompts output via the loudspeakers 317 and user voice commands input via the microphone 380.

FIG. 3b is a detailed schematic block diagram of the processor 305 and a "memory" 334. The memory 334 represents a logical aggregation of all the memory devices (including the HDD 310 and semiconductor memory 306) that can be accessed by the computer module 301 in FIG. 3a.

When the computer module 301 is initially powered up, a power-on self-test (POST) program 350 executes. The POST program 350 is typically stored in a ROM 349 of the semiconductor memory 306. A program permanently stored in a hardware device such as the ROM 349 is sometimes referred to as firmware. The POST program 350 examines hardware within the computer module 301 to ensure proper functioning, and typically checks the processor 305, the memory (309, 306), and a basic input-output systems software (BIOS) module 351, also typically stored in the ROM 349, for correct operation. Once the POST program 350 has run successfully, the BIOS 351 activates the hard disk drive 310. Activation of the hard disk drive 310 causes a bootstrap loader program 352 that is resident on the hard disk drive 310 to execute via the processor 305. This loads an operating system 353 into the RAM memory 306 upon which the operating system 353 commences operation. The operating system 353 is a system level application, executable by the processor 305, to fulfil various high level functions, including processor management, memory management, device management, storage management, software application interface, and generic user interface.

The operating system 353 manages the memory (309, 306) in order to ensure that each process or application running on the computer module 301 has sufficient memory in which to execute without colliding with memory allocated to another process. Furthermore, the different types of memory available in the system 300 must be used properly so that each process can run effectively. Accordingly, the aggregated memory 334 is not intended to illustrate how particular segments of memory are allocated (unless otherwise stated), but rather to provide a general view of the memory accessible by the computer system 300 and how such is used.

The processor 305 includes a number of functional modules including a control unit 339, an arithmetic logic unit (ALU) 340, and a local or internal memory 348, sometimes called a cache memory. The cache memory 348 typically includes a number of storage registers 344-346 in a register section. One or more internal buses 341 functionally interconnect these functional modules. The processor 305 typically also has one or more interfaces 342 for communicating with external devices via the system bus 304, using a connection 318.

The application program 333 includes a sequence of instructions 331 that may include conditional branch and loop instructions. The program 333 may also include data 332 which is used in execution of the program 333. The instructions 331 and the data 332 are stored in memory locations 328-330 and 335-337 respectively. Depending upon the relative size of the instructions 331 and the memory locations 328-330, a particular instruction may be stored in a single memory location as depicted by the instruction shown in the memory location 330. Alternately, an instruction may be segmented into a number of parts each of which is stored in a separate memory location, as depicted by the instruction segments shown in the memory locations 328-329.

In general, the processor 305 is given a set of instructions which are executed therein. The processor 305 then waits for a subsequent input, to which it reacts to by executing another set of instructions. Each input may be provided from one or more of a number of sources, including data generated by one or more of the input devices 302, 303, data received from an external source across one of the networks 320, 322, data retrieved from one of the storage devices 306, 309 or data retrieved from a storage medium 325 inserted into the corresponding reader 312. The execution of a set of the instructions may in some cases result in output of data. Execution may also involve storing data or variables to the memory 334.

The disclosed arrangements use input variables 354, that are stored in the memory 334 in corresponding memory locations 355-357. The arrangements produce output variables 361, that are stored in the memory 334 in corresponding memory locations 362-364. Intermediate variables 358 may be stored in memory locations 359, 360, 366 and 367.

The register section 344-346, the arithmetic logic unit (ALU) 340, and the control unit 339 of the processor 305 work together to perform sequences of micro-operations needed to perform "fetch, decode, and execute" cycles for every instruction in the instruction set making up the program 333. Each fetch, decode, and execute cycle comprises:

(a) a fetch operation, which fetches or reads an instruction 331 from a memory location 328;

(b) a decode operation in which the control unit 339 determines which instruction has been fetched; and (c) an execute operation in which the control unit 339 and/or the ALU 340 execute the instruction.

Thereafter, a further fetch, decode, and execute cycle for the next instruction may be executed. Similarly, a store cycle may be performed by which the control unit 339 stores or writes a value to a memory location 332.

Each step or sub-process in the processes of FIG. 2 is associated with one or more segments of the program 333, and is performed by the register section 344-346, the ALU 340, and the control unit 339 in the processor 305 working together to perform the fetch, decode, and execute cycles for every instruction in the instruction set for the noted segments of the program 333.

The methods 200 and 250 may alternatively be implemented in dedicated hardware such as one or more integrated circuits performing the functions or sub functions of the method. Such dedicated hardware may include graphic processors, digital signal processors, Field Programmable Gate Arrays (FPGA's) or one or more microprocessors and associated memories.

The foregoing describes only some embodiments of the present invention, and modifications and/or changes can be made thereto without departing from the scope and spirit of the invention, the embodiments being illustrative and not restrictive.

In the context of this specification, the word "comprising" means "including principally but not necessarily solely" or "having" or "including", and not "consisting only of". Variations of the word "comprising", such as "comprise" and "comprises" have correspondingly varied meanings.

The invention claimed is:

1. A method of detecting and identifying radioactive materials by processing a gamma ray spectrum acquired from a target while the target is in transit on a path, the method comprising:
    acquiring the gamma ray spectrum from the target while the target is in transit on the path;
    determining whether the gamma ray spectrum of the target belongs to a first set or a second set of a plurality of sets of gamma ray spectra belonging to a library comprising previously acquired spectra and an artificial gamma ray spectrum, while the target is in transit on the path, using optimal loading coefficients associated with one or more radionuclide sources of interest having gamma ray spectra belonging to the library, wherein the gamma ray spectra in the first set are spectra of only one of the radionuclide sources of interest, and the gamma ray spectra in the second set are the artificial gamma ray spectrum and spectra only of radionuclide sources of interest other than the gamma ray spectra in the first set, wherein the optimal loading coefficients have been obtained using Fisher linear discriminant analysis by:
        computing a between-set scatter matrix and a within-set scatter matrix for the gamma ray spectra in the first set and the second set; and
        computing the optimal loading coefficients from generalized eigenvector corresponding to largest generalized eigenvalue of the between-set and within-set scatter matrices;
    repeating the determining for each radionuclide source of interest having gamma ray spectra in the library;
    generating an output signal dependent on the repeated determining; and
    operating a preventative measure on the path of the target based on the output signal; wherein:
        the artificial gamma ray spectrum which comprises one of (i) a constant value with an additive Gaussian noise component and (ii) a quasi-linear spectrum with the additive Gaussian noise component.

2. The method according to claim 1, wherein the determining whether the gamma ray spectrum of the target belongs to the first set is carried out within a region of interest of the gamma ray spectra belonging to the first set.

3. The method according to claim 1, wherein the determining whether the gamma ray spectrum of the target belongs to the first set comprises:
    a. computing a distance between the gamma ray spectrum of the target projected by the optimal loading coefficients and the second set containing further gamma ray spectra of further radionuclide sources projected by the optimal loading coefficients; and
    b. determining whether the gamma ray spectrum of the target belongs to the first set using the computed distance.

4. The method according to claim 3, wherein the determining comprises determining whether the computed distance is above a threshold distance.

5. The method according to claim 4, further comprising determining the threshold distance using the steps of:
    a. determining mean gross counts in the second set;
    b. estimating standard deviation of the second set using a power law relationship with the mean gross counts; and
    c. determining the threshold distance as a predetermined number of standard deviations of the second set.

6. The A method according to claim 3, wherein the computed distance is a Mahalanobis distance.

7. The method according to claim 3, wherein the computed distance is a Euclidean distance.

8. The method according to claim 3, further comprising, if the gamma ray spectrum of the target is determined to belong to the first set, estimating intensity of the only one radionuclide sources of interest in the target based on the computed distance.

9. The method according to claim 1, further comprising pre-processing the gamma ray spectrum of the target before determining whether the gamma ray spectrum of the target belongs to the first set, wherein the pre-processing comprises one or more of the following:
  a. intensity normalization; and
  b. spectrum standardization.

10. The method according to claim 1, further comprising pre-processing the gamma ray spectra in each set before computing the between-set and within-set scatter matrices, wherein the pre-processing comprises one or more of the following:
  a. intensity normalization; and
  b. spectrum standardization.

11. The method according to claim 1, wherein the generating comprises generating the output signal if the gamma ray spectrum of the target is determined to belong to the first set.

12. The method according to claim 1, wherein the preventative measure includes activating an alarm in response to the generated output signal.

13. The method according to claim 1, further comprising acquiring the gamma ray spectrum of the target as the target passes through a detection zone.

14. The method according to claim 13, wherein the acquiring is performed without the target stopping in the detection zone.

15. The method according to claim 13, wherein the gamma ray spectrum of the target is acquired in less than about 10 seconds.

16. The method according to claim 13, wherein the gamma ray spectrum of the target is acquired by means of a portable gamma ray detector.

17. The method of claim 1, wherein the path is from a first point to a second point, the preventative measure is operating a barrier, wherein the barrier is located at or before the second point on the path.

18. The method of claim 1, wherein the target moves on the path between a first point and a second point.

19. The method of claim 1, wherein the target remains stationary on the path between a first point and a second point for a limited period of time.

20. An apparatus for detecting and identifying radioactive materials of a target while the target is in transit on a path, the apparatus comprising:
  a gamma ray detector configured to acquire a gamma ray signal from the target while the target is in transit on the path;
  an amplifier configured to amplify the gamma ray signal acquired by the gamma ray detector to thereby form an amplified gamma ray signal;
  a multichannel analyzer configured to partition the amplified gamma ray signal into energy bins, thereby generating a gamma ray spectrum;
  a memory configured to store the generated gamma ray spectrum, and
  a processor configured to execute computer program code to cause the processor to perform a method of detecting and identifying radioactive materials by processing the gamma ray spectrum of the target while the target is in transit on the path, the computer program code comprising:
    code for acquiring the gamma ray spectrum from the target while the target is in transit on the path;
    code for determining whether the gamma ray spectrum of the target belongs to a first set or a second set of a plurality of sets of gamma ray spectra belonging to a library comprising previously acquired spectra and an artificial gamma ray spectrum, while the target is in transit on the path, using optimal loading coefficients associated with one or more radionuclide sources of interest having gamma ray spectra belonging to the library, wherein the gamma ray spectra in the first set are spectra of only one of the radionuclide sources of interest, and the gamma ray spectra in the second set are the artificial gamma ray spectrum and spectra only of radionuclide sources of interest other than the gamma ray spectra in the first set, wherein the optimal loading coefficients have been obtained using Fisher linear discriminant analysis by:
      computing a between-set scatter matrix and a within-set scatter matrix for the gamma ray spectra in the first set and the second set; and
      computing the optimal loading coefficients from generalized eigenvector corresponding to largest generalized eigenvalue of the between-set and within-set scatter matrices;
    code for repeating the determining for each radionuclide source of interest having gamma ray spectra in the library;
    code for generating an output signal dependent on the repeated determining; and
    code for operating a preventative measure on the path of the target based on the output signal, wherein:
    the artificial gamma ray spectrum comprises one of (i) a constant value with an additive Gaussian noise component and (ii) a quasi-linear spectrum with the additive Gaussian noise component.

21. A non-transitory tangible computer readable storage medium having a computer program recorded thereon, the computer program being executable by a computer apparatus to cause the computer apparatus to execute a method of detecting and identifying radioactive materials by processing a gamma ray spectrum acquired from a target while the target is in transit on a path, said computer program comprising:
  code for acquiring the gamma ray spectrum from the target while the target is in transit on the path;
  code for determining whether the gamma ray spectrum of the target belongs to a first set or a second set of a plurality of sets of gamma ray spectra belonging to a library comprising previously acquired spectra and an artificial gamma ray spectrum, while the target is in transit on the path using optimal loading coefficients associated with one or more radionuclide sources of interest having gamma ray spectra belonging to the library, wherein the gamma ray spectra in the first set are spectra of only one of the radionuclide sources of interest, and the gamma ray spectra in the second set are the artificial gamma ray spectrum and gamma ray spectra only of radionuclide sources of interest other than the gamma ray spectra in the first set, wherein the optimal loading coefficients have been obtained using Fisher linear discriminant analysis by:

computing a between-set scatter matrix and a within-set scatter matrix for the gamma ray spectra in the first set and the second set; and computing the optimal loading coefficients from generalized eigenvector corresponding to largest generalized eigenvalue of the between-set and within-set scatter matrices;

code for repeating the determining for each radionuclide source of interest having gamma ray spectra in the library;

code for generating an output signal dependent on the repeated determining; and code for operating a preventative measure on the path of the target based on the output signal, wherein:

the artificial gamma ray spectrum comprises one of (i) a constant value with an additive Gaussian noise component and (ii) a quasi-linear spectrum with the additive Gaussian noise component.

* * * * *

UNITED STATES PATENT AND TRADEMARK OFFICE
CERTIFICATE OF CORRECTION

PATENT NO. : 10,539,693 B2
APPLICATION NO. : 14/131642
DATED : January 21, 2020
INVENTOR(S) : David Boardman Page 1 of 1

It is certified that error appears in the above-identified patent and that said Letters Patent is hereby corrected as shown below:

On the Title Page

Item (73) Assignee:
Please change Assignee from "Australian Nuclear Science and Technology Organization" to
-- Australian Nuclear Science and Technology Organisation --.

Signed and Sealed this
Sixteenth Day of June, 2020

Andrei Iancu
*Director of the United States Patent and Trademark Office*